United States Patent [19]

Sheppard et al.

[11] Patent Number: 5,463,076

[45] Date of Patent: Oct. 31, 1995

[54] METHOD OF MAKING MULTIDIMENSIONAL OLIGOMERS

[75] Inventors: Clyde H. Sheppard, Bellevue, Wash.; Hyman R. Lubowitz, Rolling Hills Estates, Calif.

[73] Assignee: The Boeing Company, Seattle, Wash.

[21] Appl. No.: 38,750

[22] Filed: Mar. 26, 1993

Related U.S. Application Data

[60] Division of Ser. No. 605, Jan. 5, 1987, Pat. No. 5,210,213, which is a continuation-in-part of Ser. No. 810,817, Dec. 17, 1985, abandoned, which is a continuation-in-part of Ser. No. 726,258, Apr. 23, 1985, abandoned, which is a continuation-in-part of Ser. No. 519,394, Aug. 1, 1983, abandoned, and a continuation-in-part of Ser. No. 673,229, Nov. 20, 1984, Pat. No. 4,584,364, and a continuation-in-part of Ser. No. 536,350, Sep. 27, 1983, abandoned, and a continuation-in-part of Ser. No. 505,348, Jun. 17, 1983, Pat. No. 4,536,559, and a continuation-in-part of Ser. No. 651,826, Sep. 18, 1984, abandoned, which is a continuation-in-part of Ser. No. 536,350, Sep. 27, 1983, abandoned, and a continuation-in-part of Ser. No. 576,790, Feb. 6, 1984, abandoned, and a continuation-in-part of Ser. No. 505,348, Jun. 17, 1983, Pat. No. 4,536,559, said Ser. No. 673,229, is a continuation of Ser. No. 576,790, Feb. 6, 1984, abandoned, which is a continuation-in-part of Ser. No. 321,119, Nov. 13, 1981, abandoned, said Ser. No. 536,350, is a continuation-in-part of Ser. No. 519,394, Aug. 1, 1983, abandoned.

[51] Int. Cl.$^6$ ............... C07D 403/12; C07D 519/00
[52] U.S. Cl. ............... 548/431; 548/435; 548/462; 548/521
[58] Field of Search ............ 548/431, 435, 548/462, 521; 568/322, 323, 636

[56] References Cited

U.S. PATENT DOCUMENTS

| | | | |
|---|---|---|---|
| 3,998,786 | 12/1976 | D'Alelio | 428/474 |
| 4,055,543 | 10/1977 | D'Alelio | 428/474 |
| 4,075,171 | 2/1978 | D'Alelio | 428/474 |
| 4,251,417 | 2/1981 | Chow et al. | 528/172 |
| 4,251,418 | 2/1981 | Chow et al. | 560/13 |
| 4,251,420 | 2/1981 | Antonoplos et al. | 562/427 |
| 4,299,946 | 11/1981 | Balme et al. | 528/125 |
| 4,381,363 | 4/1983 | Reinhart | 528/125 |
| 4,418,181 | 11/1983 | Monacelli | 548/521 |
| 4,438,280 | 3/1984 | Monacelli | 562/457 |
| 4,460,783 | 7/1984 | Nishikawa et al. | 548/462 |
| 4,684,714 | 8/1987 | Lubowitz et al. | 528/353 |
| 4,737,550 | 4/1988 | Tomalia | 525/418 |
| 5,210,213 | 5/1993 | Sheppard et al. | 548/435 |

FOREIGN PATENT DOCUMENTS 1210408  8/1989  Japan.

OTHER PUBLICATIONS

March, Advanced Organic Chemistry: Reactions, Mechanisms and Structure, McGraw–Hill, New York (1968) pp. 413, 414, 500.

Worthy et al, Chem. and Eng. News., Feb. 22, 1988, pp. 19–21.

Tomalia et al, Polymer Journal, vol. 17, No. 1 (1988) pp. 117–132.

*Primary Examiner*—Richard L. Raymond
*Attorney, Agent, or Firm*—John C. Hammar

[57] ABSTRACT

Multidimensional oligomers of the present invention are surprisingly useful for advanced composites because each generally has a use temperature greatly in excess of its curing temperature. The oligomers have essentially no arms, and comprise crosslinking phenylimide end caps condensed directly onto an aromatic hub (preferably, phenyl) through "commodity" polymeric linkages, such as amide, diimide, ether, or ester. For example, p-nadicimidobenzoylchloride can be condensed with triaminobenzene to yield a multidimensional, crosslinking amide oligomer. Short chains of ether/carbonyl aromatic chains can be included, if desired. Methods for making these high-performance oligomers with ether/carbonyl aromatic chains use an Ullmann ether synthesis followed by a Friedel-Crafts reaction.

2 Claims, No Drawings

METHOD OF MAKING MULTIDIMENSIONAL OLIGOMERS

REFERENCE TO RELATED APPLICATIONS

The present invention is a divisional application of Ser. No. 000,605, Jan. 5, 1987, U.S. Pat. No. 5,210,213, which is a continuation-in-part application of U.S. patent application Ser. No. 810,817, filed Dec. 17, 1985, abandoned; which itself was a continuation-in-part application of U.S. Ser. No. 726,258, filed Apr. 23, 1985, abandoned; which itself was a continuation-in-part of the following five United States Patent Applications:

(a) U.S. Ser. No. 519,394, filed Aug. 1, 1983, now abandoned; and (b) U.S. Ser. No. 673,229, filed Nov. 20, 1984, (now U.S. Pat. No. 4,584,364, issued Apr. 22, 1986), which itself was a continuation of U.S. Ser. No. 576,790, filed Feb. 6, 1984, now abandoned, which itself was a continuation-in-part application of U.S. Ser. No. 321,119, filed Nov. 13, 1981, now abandoned; and (c) U.S. Ser. No. 536,350, filed Sep. 27, 1983, now abandoned, which itself was a continuation-in-part application of U.S. Ser. No. 519,394, filed Aug. 1, 1983, now abandoned; and (d) U.S. Ser. No. 505,348, filed Jun. 17, 1983, now U.S. Pat. No. 4,536,559; and (e) U.S. Ser. No. 651,826, filed Sep. 18, 1984, abandoned, which is a continuation-in-part application of the following three U.S. patent applications:

U.S. patent application Ser. No. 536,350, filed Sep. 27, 1983, abandoned;

U.S. patent application Ser. No. 576,790, filed Feb. 6, 1984, abandoned; and

U.S. patent application Ser. No. 505,348, filed Jun. 17, 1983, now U.S. Pat. No. 4,536,559.

TECHNICAL FIELD

The present invention relates to multidimensional oligomers that include a hub and a plurality of radiating arms, each arm terminating at the periphery in a crosslinking end cap moiety. Such compounds have relatively low molecular weight, but cure to high performance composites useful at high temperatures.

BACKGROUND ART

Epoxies dominate the composite industry today primarily because they are relatively low-cost and are easy to use. Epoxies, however, have low thermal stabilitites and tend to be brittle. There is a need for high performance, temperature-resistant composites made curing inexpensive, "commodity" starting materials that will be useful in conditions where epoxies cannot be used. The present invention describes oligomers that fulfill these requirements and present great promise for engineering composites, particularly for aerospace applications.

SUMMARY OF THE INVENTION

Composites possessing glass transition temperatures greatly in excess of their curing temperatures can be prepared from multidimensional oligomers formed by the condensation of "commodity" starting materials. The oligomers have the general formula:

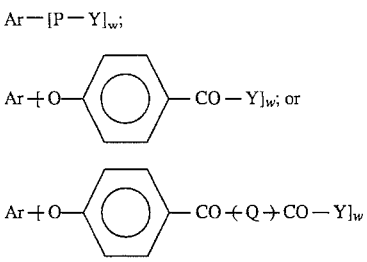

wherein
w=an integer greater than 2 and not greater than the available number of substitutable hydrogens on the Ar group;
Ar=an aromatic moiety;
P=amide, ether, ester, or

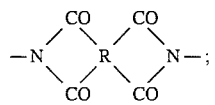

Y=

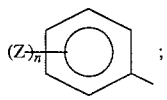

n=1 or 2;
Z=

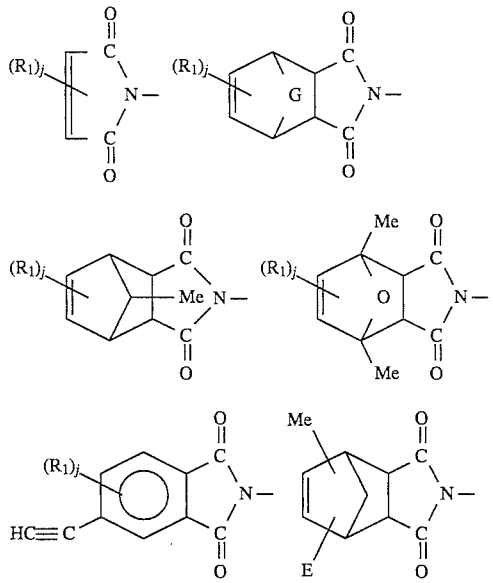

R=an organic radical having a valence of four;

$R_1$=any of lower alkyl, lower alkoxy, aryl, phenyl, or substituted aryl (including hydroxyl or halo-substituents);

j=0, 1, or 2;

E=allyl or methallyl;

G=—$CH_2$—, —S—, —O—, or —$SO_2$—;

Q=an organic radical of valence two, and preferably a compound selected from the group consisting of:

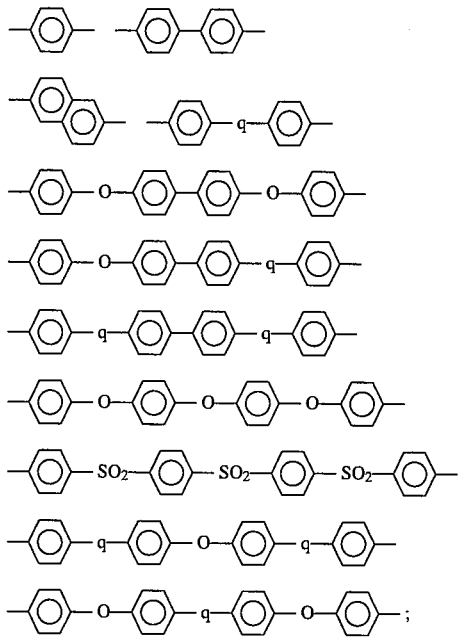

q=—$SO_2$—, —CO—, —S—, or —$(CF_3)_2C$—, and preferably —$SO_2$— or —CO—.

As will be explained, these oligomers are prepared by the condensation of an aromatic hub and a suitable end cap moiety with or without a chain-extending group (Q) to provide short-armed, multidimensional oligomers of high thermal stability.

BEST MODE CONTEMPLATED FOR MAKING AND USING THE INVENTION

Multidensional morphologies in crosslinking oligomers produce composites having solvent resistance, high glass transition temperatures, and toughness upon curing. The resins and prepregs are readily processed prior to curing. The cured composites have glass transition temperatures (melt temperatures) in excess of their curing temperatures. Such compounds can be readily made from "commodity" starting materials that are readily available at relatively low cost. The composites are cost competitive with epoxies, but possess better physical properties for aerospace applications (especially higher use temperatures).

Particularly perferred oligomers of the present invention have the general formula:

Ar—[P—Y]$_w$ wherein

Ar=an aromatic radial;

Y=a crosslinking end cap;

w=an integer greater than 2 and not greater than the available number of substitutable hydrogens on the Ar group;

P=—CONH—, —NHCO—, —O—,

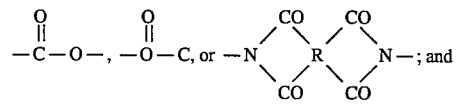

R=an organic radical having a valency of four, and, preferably, a residue of pyromellitic dianhydride, benzophenonetetracarboxylic dianhydride, or 5-(2,4-diketotetrahydrofuryl)-3-methyl-3-cyclohexene-1,2-dicarboxylic anhydride The crosslinking end cap (Y) is preferably a phenylimide having a formula:

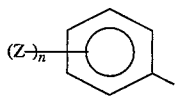

wherein n=1 or 2;

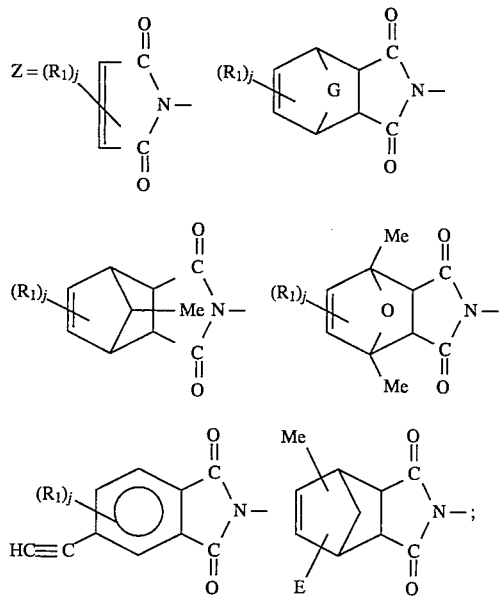

$R_1$=any of lower alkyl, lower alkoxy, aryl, or substituted aryl (including hydroxyl or halo- on any replaceable hydrogen);

j=0, 1, or 2; and

G=—$CH_2$—, —S—, —O—, or —$SO_2$—.

The most preferred end caps include:

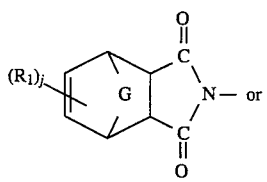

-continued

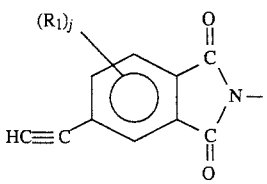

wherein
n=1 of 2 (preferably 2);
j=0, 1, or 2 (preferably 1);
G and $R_1$ are as previously defined (with $R_1$ preferably being

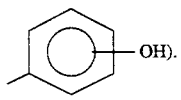

These multidimensional oligomers are made by the condensation of aromatic hub monomers with the end cap reactants in an inert atmosphere. For example, the hub might be

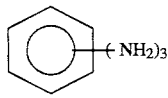

and the end cap, a radical as illustrated above terminated with an acid halide to form an amide linkage (NHCO) between the hub and the end cap. Alternatively, the hub might include the acid halide and the end cap the amine so that the condensation will yield an amide of opposite orientation (CONH). Ester or ether multidimensional oligomers of this general type are made in accordance with Examples I through VII of our copending application U.S. Ser. No. 810,817 by reacting an acid halide and a phenol. Diimide linkages are formed by reacting an amine-terminated hub with a dianhydride and an amine-terminated end cap.

The hub (Ar) precursor preferably is selected from the group consisting of phenyl, naphthyl, biphenyl, azalinyl (including melamine radicals) amines or acid halides, or triazine derivatives described in U.S. Pat. No. 4,574,154 (incorporated by reference) to Okamoto of the general formula:

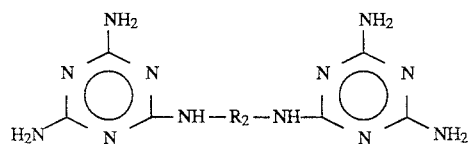

wherein $R_2$ is a divalent hydrocarbon residue containing 1–12 carbon atoms (and, preferably, ethylene).

Substantially stoichiometric amounts of the reactants are usually mixed together in a suitable solvent under an inert atmosphere to achieve the condensation. The reaction mixture may be heated, as necessary, to complete the reaction. Any of the oligomers can be used to form prepregs by application of the oligomers in a suitable solvent to suitable prepregging materials, and the prepregs can be cured in conventional vacuum bagging techniques at elevated temperatures to produce composites that have use temperatures in excess of their cure temperatures. The crosslinking end caps apparently bind the composites into a complex, 3-dimensional network upon curing by chemical induction or heating to yield a product having high thermal stability than the core temperature.

Compounds of the formulae:

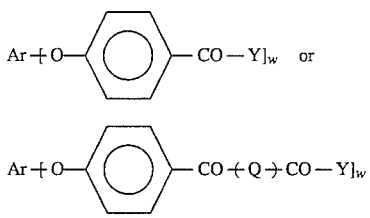

can also be synthesized with an Ullmann ether synthesis followed by a Friedel Crafts reaction, as will be further explained. Here, Q=

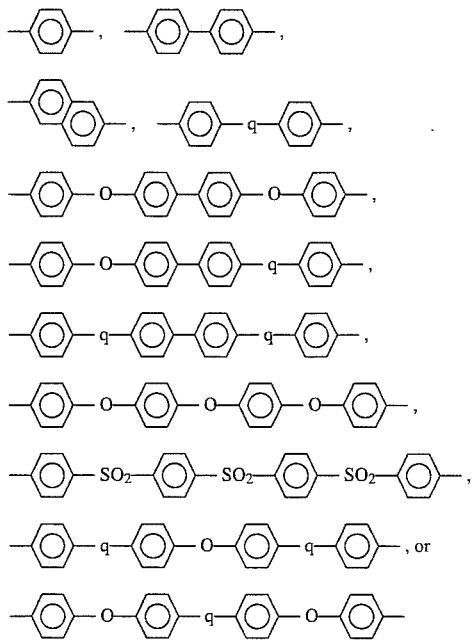

wherein
q=—$SO_2$—, —CO—, —S—, or —$(CF_3)_2C$—, and preferably —$SO_2$— or —CO—.

To form the

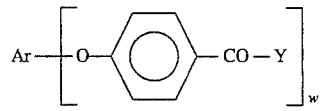

compounds, preferably a halo-substituted hub is reacted with phenol in DMAC with a base (NaOH) over a Cu Ullmann catalyst to produce an ether "star" with active hydrogens para- to the either linkages. End caps terminated with acid halide functionalities can react with these active aryl groups in a Friedel Crafts reaction to yield the desired product. For example, 1 mole of trichlorobenzene can be reacted with about 3 moles of phenol in the Ullmann ether reaction to yield an intermediate of the general formula:

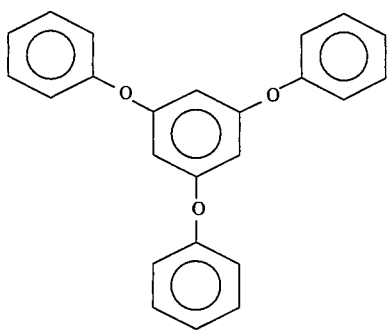

This intermediate can, then, be reacted with about 3 moles of (Y)-COCl to produce the final, crosslinkable, ether/carbonyl oligomer.

Similarly to form the

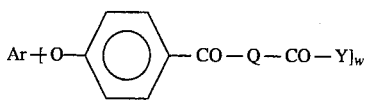

compounds, the hub is extended preferably by reacting a halo-substituted hub with phenol in the Ullmann ether synthesis to yield the ether intermediate of the

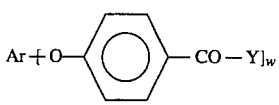

compounds. This intermediate is mixed with the appropriate stoichiometric amounts of a diacid halide of the formula XOC—Q—COX and an end cap of the formula

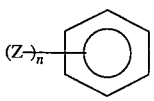

in the Friedel Crafts reaction to yield the desired, chain-extended ether/carbonyl star and star-burst oligomers.

The end caps (Z) crosslink at different temperatures (i.e., their unsaturation is activated at different curing temperatures), so the cap should be selected to provide cured composites of the desired thermal stability. That is the backbone of the oligomer should be stable to at least the cure temperature of the caps. The multidimensional morphology allows the oligomers to be cured at a temperature far below the use temperature of the resulting composite, so completely aromatic backbones connected by heteroatoms are preferred to enhance the thermal stability.

U.S. Pat. No. 4,604,437 is incorporated by reference. That patent describes a polymer made from substituted, unsaturated, bicyclic imides having end caps of the formula:

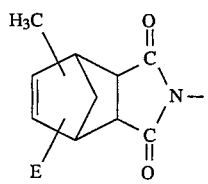

wherein

E=allyl or methallyl, and n=1 or 2.

These bicyclic imide end caps are prepared from the analogous anhydride by condensation with an amine, and provide oligomers that cure in a temperature range between DONA (dimethyloxynadic) and nadic caps.

While essentially any dianhydride (aliphatic or aromatic can be used to form the diimide oligomers of the present invention, aromatic dianhydrides, such as pyromellitic dianhydride or benzophenonetetracarboxylic dianhydride, are preferred for cost, convenience, and thermal stability in the cured composite. If an aliphatic dianhydride is used, preferably the dianhydride is 5-(2,4-diketotetrahydrofuryl)-3-methyl-3-cyclohexene-1,2-dicarboxylic anhydride (MCTC).

End caps of the formula

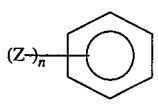

are prepared by reacting an amine-substituted benzene, such as aniline, with an anhydride in the manner outlined in U.S. Pat. No. 4,604,437. One process for making the precursor anhydrides is described in U.S. Pat. No. 3,105,839.

While preferred embodiments have been shown and described, those of ordinary skill in the art will recognize variation, modifications, or alterations that might be made to the embodiments that are described without departing from the inventive concept. Accordingly, the description should be interpreted liberally, and the claims should not be limited to the described embodiments, unless such limitation is necessary to avoid the pertinent prior art.

We claim:

1. A method for making an oligomer of the general formula:

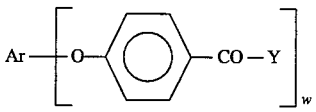

wherein

Ar=an aromatic moiety selected from the group consisting of phenyl, biphenyl, naphthyl, and azalinyl;

w=3 or 4;

Y=

5,463,076

$(Z)_n$—⟨phenyl⟩;

n=1 or 2;

[structures showing maleimide, G-bridged imide, methylated norbornene imide, oxa-bridged imide, ethynyl phthalimide, and E-substituted bicyclic imide]

$R_1$=any of lower alkyl, lower alkoxy, or aryl;

j=0, 1, or 2;

G=—CH$_2$—, —S—, —O—, or —SO$_2$—,

Me=methyl; and

E=allyl or methallyl, comprising the steps of:

(a) reacting Ar—(X)$_w$ with at least w moles of phenol in an Ullmann ether synthesis in DMAC and a base in the presence of an Ullmann copper catalyst to form an Ar— ether intermediate; and (b) reacting the Ar— ether intermediate with at least w moles of Y—COX under Friedel-Crafts conditions in a suitable solvent to produce the oligomer, wherein X=halogen.

2. A method for making an oligomer of the general formula:

$$Ar\{-O-\langle phenyl \rangle -CO-Q-CO-Y\}_w$$

wherein

Ar=an aromatic moiety selected from the group consisting of phenyl, biphenyl, naphthyl, and azalinyl;

w=3 or 4;

Y=

$(Z)_n$—⟨phenyl⟩;

n=1 or 2;

Z=

[structures showing maleimide, G-bridged imide, methylated norbornene imide, oxa-bridged imide, ethynyl phthalimide, and E-substituted bicyclic imide]

Me=methyl;

E=allyl or methallyl;

Q=an organic, divalent radical selected from the group consisting of:

—⟨phenyl⟩—, —⟨phenyl⟩—⟨phenyl⟩—,

—⟨naphthyl⟩—, —⟨phenyl⟩—q—⟨phenyl⟩—,

—⟨phenyl⟩—O—⟨phenyl⟩—⟨phenyl⟩—O—⟨phenyl⟩—,

—⟨phenyl⟩—O—⟨phenyl⟩—⟨phenyl⟩—q—⟨phenyl⟩—,

—⟨phenyl⟩—q—⟨phenyl⟩—⟨phenyl⟩—q—⟨phenyl⟩—,

—⟨phenyl⟩—O—⟨phenyl⟩—O—⟨phenyl⟩—O—⟨phenyl⟩—,

—⟨phenyl⟩—SO$_2$—⟨phenyl⟩—SO$_2$—⟨phenyl⟩—SO$_2$—⟨phenyl⟩—,

—⟨phenyl⟩—q—⟨phenyl⟩—O—⟨phenyl⟩—q—⟨phenyl⟩—,

—⟨phenyl⟩—O—⟨phenyl⟩—q—⟨phenyl⟩—O—⟨phenyl⟩—, q=—SO$_2$—, —CO—, —S—, or —(CF$_3$)$_2$C—;

$R_1$=any of lower alkyl, lower alkoxy, or aryl;

X=halogen;

j=0, 1, or 2; and

G=—$CH_2$—, —S—, —O—, or —$SO_2$—, comprising the steps:
- (a) reacting Ar—$(X)_w$ with at least w moles of phenol in an Ullmann ether synthesis in DMAC and a base and in the presence of an Ullmann copper catalyst to form an Ar— ether intermediate; and
- (b) reacting the Ar— ether intermediate with at least w moles of a diacid halide of the general formula XOC—Q—COX and with at least w moles of

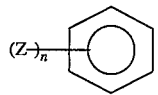

under Friedel-Crafts conditions in a suitable solvent to produce the oligomer.

* * * * *